United States Patent [19]

Berggren et al.

[11] Patent Number: 5,036,868
[45] Date of Patent: Aug. 6, 1991

[54] ANASTOMOSIS PREPARATION TECHNIQUE

[75] Inventors: Anders Berggren, Linkoping; Hakan Rohman, Mantorp; Rafn Ragnarsson, Linkoping, all of Sweden

[73] Assignee: Unilink Inc., Centreville, Va.

[21] Appl. No.: 578,544

[22] Filed: Sep. 6, 1990

Related U.S. Application Data

[63] Continuation of Ser. No. 471,706, Jan. 29, 1990, abandoned, which is a continuation of Ser. No. 235,882, Aug. 18, 1988, abandoned.

[51] Int. Cl.$^5$ ............. A61B 19/00; A61M 29/00
[52] U.S. Cl. ............... 128/898; 606/192; 606/194; 604/96; 604/104
[58] Field of Search ......... 606/196, 198, 191–194; 604/94–104; 128/898

[56] References Cited

U.S. PATENT DOCUMENTS

| | | | |
|---|---|---|---|
| 3,050,066 | 8/1962 | Koehn | 606/192 |
| 3,438,375 | 4/1969 | Ericson . | |
| 3,516,408 | 6/1970 | Montanti | 604/96 |
| 4,230,119 | 10/1980 | Blum | 604/194 |
| 4,447,227 | 5/1984 | Kotsanis | 604/96 |
| 4,523,592 | 6/1985 | Daniel . | |
| 4,547,187 | 10/1985 | Kelly | 604/97 |
| 4,733,665 | 3/1988 | Palmaz | 604/96 |
| 4,950,238 | 8/1990 | Sullivan | 604/101 |

FOREIGN PATENT DOCUMENTS

WO82/01644 5/1982 PCT Int'l Appl. .
1538737 1/1979 United Kingdom .

Primary Examiner—Stephen C. Pellegrino
Assistant Examiner—Gary Jackson
Attorney, Agent, or Firm—Synnestvedt & Lechner

[57] ABSTRACT

This invention provides a surgical method for minimizing constrictions in a vessel in a joint area at the site of an anastomotic ring placement. The method includes inserting an upper part of a hollow, T-shaped member through an incision in a vessel. The T-shaped member includes a vertical part comprising a pipe or hose and an upper part which is more elastic than the vertical part and consists essentially of an expansible elongated balloon in an unexpanded state. The elongated balloon is an open communication with the hollow vertical part and can be expanded by pressurizing with a pressure medium through the vertical part into the upper part so as to expand the upper part and thereby substantially uniformly deform a portion of the joined area of the vessel. The method also includes depressurizing the upper part by removing the pressure medium and allowing the upper part to return to its unexpanded state and then removing the upper part from the vessel prior to attachment of an anastomotic ring to the vessel.

5 Claims, 1 Drawing Sheet

ANASTOMOSIS PREPARATION TECHNIQUE

Cross Reference to Related Applications

The present application is a continuation of U.S. Ser. No. 471,706 abandoned, filed on Jan. 29, 1990, which in turn, is a continuation of U.S. Ser. No. 235,882 abandoned, filed on Aug. 18, 1988, as a U.S. National patent application, which is a result of the completion of the P.C.T. phase of P.C.T. Ser. No. PCT/SE87/00596, filed on Dec. 11, 1987. The P.C.T. application claims priority based on Swedish patent application, Serial No. 8605455-8, filed on Dec. 18, 1986. All of these applications were filed in the name of the present inventors and are assigned to the Assignee of the instant application. Furthermore, all of these applications are incorporated herein by reference in their entirety.

Field of the Invention

This invention relates to anastomotic preparation techniques, and in particular, to a method for minimizing constrictions in blood vessels at the sight of branching during anastomotic ring placement.

BACKGROUND OF THE INVENTION

In vessel surgery, it has become increasingly useful to use by-passes, for example, constricted vessels can be replaced by healthier ones that are coupled in parallel or connected to other vessel locations. Until now, vessels have been joined with a common technique of sewing the vessels together with sutures.

More recently, anastomosis rings have become available for joining blood vessels, for example, in end-to-side anastomosis. This technique is accomplished by puncturing a small cut in a first blood vessel, which is then flared and placed over the pins of an anastomosis ring. The flared joint can then be attached with a complementary anastomosis ring to the end of a second vessel. In this way, it is possible to conduct a branching or by-passing procedure in considerably less time than with conventional suturing techniques. The use of anastomosis rings, in this fashion, is known to diminish the risks to the patient and conserve resources.

Regretfully, the use of anastomosis rings for end-to-side joining of blood vessels is not entirely without draw backs. It has been found that the application of the anastomosis rings to a vessel steals material from the vessel and results in a constriction in its diameter. This is undesirable, since one of the objectives of a by-pass is to improve flow, and not to replace one impedance to flow with another. Accordingly, there is a need for a technique and instrument for eliminating constrictions caused by anastomotic ring placement.

SUMMARY OF THE INVENTION

In accordance with the present invention, a procedure has been developed for minimizing constrictions in a vessel in a joint area at the sight of anastomotic ring placement. The procedure includes inserting an upper part of a hollow, T-shaped member through an incision in the vessel. The T-shaped member includes a vertical part comprising a pipe or hose and an upper part, which is more elastic than the vertical part, which consists essentially of an expansible elongated balloon in an unexpanded state. The elongated balloon is in open communication with the hollow vertical part. The method also includes pressurizing the hollow portion of the upper part by forcing a pressure medium through the vertical part into the upper part so as to expand the upper part and thereby substantially uniformly deform a portion of the joint area of the vessel. After the vessel has been deformed, the upper part is depressurized by removing the pressure medium, which allows the upper part to return to its unexpanded state. The upper part of the T-shaped member is then removed from the vessel prior to attachment of an anastomotic ring.

Accordingly, constrictions are minimized in the vessel and a more successful by-pass or branching operation can be performed. It is believed that the surgical instrument of this invention can provide additional surface area of vessel material for attachment of the anastomotic ring, thereby avoiding a reduction in diameter of the vessel during the surgical procedure.

BRIEF DESCRIPTION OF THE DRAWINGS

The accompanying drawings illustrate an preferred embodiment of the invention, as well as other information pertinent to the disclosure, and in which.

DETAILED DESCRIPTION OF THE INVENTION

In accordance with this invention, a T-shaped instrument is provided having an elastically expansible upper part that includes a piece of a thin-walled hose, and a vertical part which can include another hose connected to a pressure source. The pressure source can conveniently be supplied by a common injection syringe. By pressurizing the elastic upper part of the T-shaped instrument, the upper part can be expanded to stretch the vessel wall, and by evacuating the upper part, it can be made very thin and easier to handle.

The two branches of the upper part of the T-shaped instrument can be inserted longitudinally within the vessel through a small cut or incision at the site of branching in the vessel. Once inserted, the upper part of the instrument is preferably expanded and the vessel can be expanded to about twice its original diameter. The pressure medium in the upper part of the instrument can then be evacuated to permit facilitated removal of the instrument from the vessel prior to applying anastomotic rings. The vessel can then, for example, be joined to the end of a second vessel to provide end-to-side anastomosis.

Since the vessel stretched with the T-shaped instrument of this invention is not entirely elastic, it will retain its expansion for a sufficient time for minimizing constrictions during the application of anastomotic rings. Moreover, tests have demonstrated that the uniform stress created by the upper part of the T-shaped instrument minimizes the incidence of rupturing or tearing of the incision in the vessel during expansion. This represents a benefit over other attempts to expand the vessel by means of pincettes, or the like.

Figure 1:
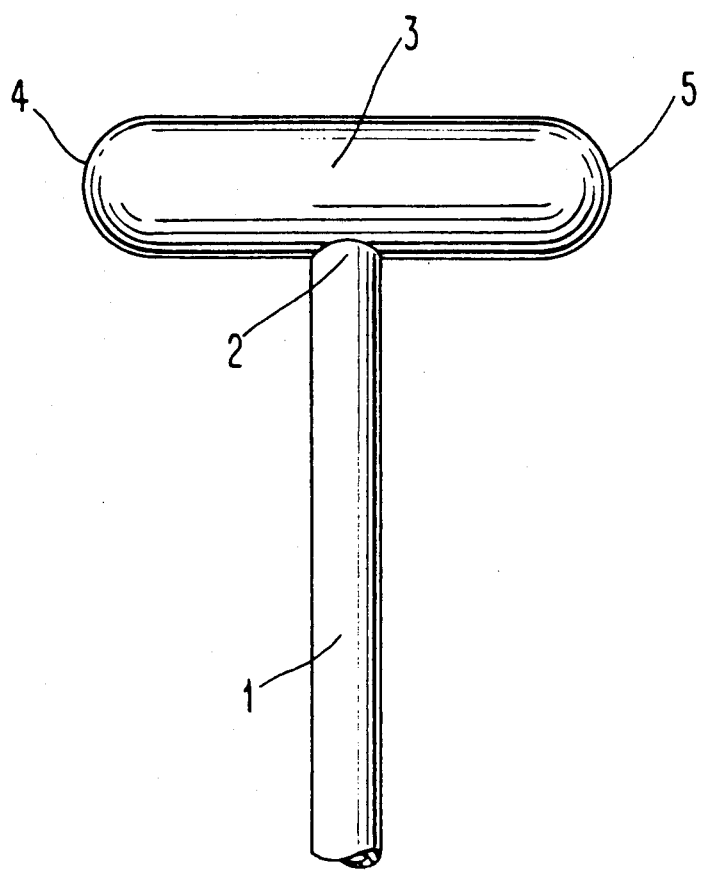
FIG. 1: is a side elevation of a preferred T-shaped instrument of this invention, illustrating an unexpanded upper part.
Figure 2:
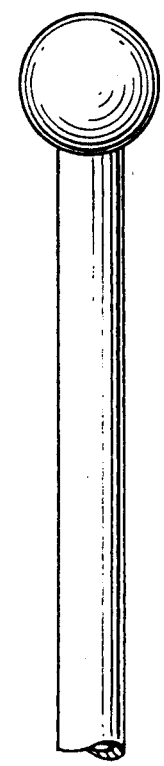
FIG. 2: is a end view of the preferred T-shaped instrument of FIG. 1.

With reference to FIG. 1, there is shown a preferred embodiment in accordance with this invention. The instrument shown in FIG. 1 includes a thick-walled connection hose 1 of plastic, which has been welded to a side opening 2 in a thin-walled elastic plastic hose 3. The hose 3 includes end portions 4 and 5 which can be welded together. The hose 1 is very thin and preferably includes a diameter that fits on a tip of an injection syringe.

Figure 3:
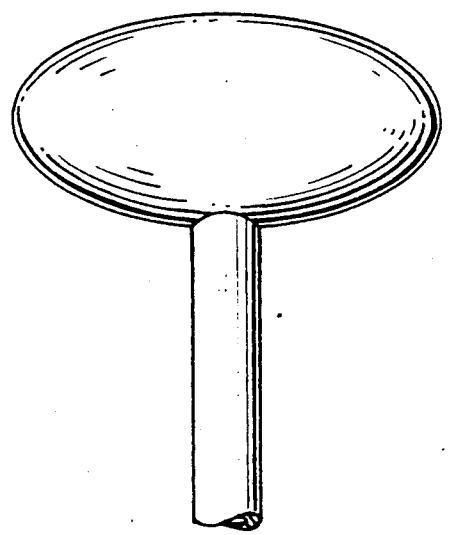
FIG. 3: illustrates another side view of the preferred T-shaped instrument of FIG. 1, illustrating how the upper part can be subjected to a pressure medium resulting in an expanded state.

In FIG. 3, the instrument has been subjected to a pressure medium from the syringe or other source. As illustrated, the thin-walled upper part 3 of the instrument has been expanded.

Although the figures show the instrument in large detail, the diameter of the connection hose 1 is preferably about 1 mm, and the upper part also referred to as the "balloon part" has a preferred diameter of about 2 mm and a preferred length of about 8 mm in the unaffected or unpressurized state.

From the foregoing, it has been demonstrated that this invention provides a very hygienic and economic surgical instrument for expanding blood vessels at the site of anastomotic ring placement. Although various embodiments have been illustrated, this was for the purpose of describing, but not limiting, the invention. Various modifications, which will become apparent to one skilled in the art, are within the scope of the invention described in the attached claims.

What is claimed is:

1. A method for minimizing constrictions in a vessel in a joint area comprising:
    inserting an upper part of a hollow, T-shaped member through an incision in said vessel, the T-shaped member including a vertical part comprising a pipe or hose, the upper part being more elastic than the vertical part and consisting essentially of an expansible elongated balloon in an unexpanded state, said elongated balloon being in open communication with the hollow vertical part;
    pressurizing the hollow portion of the upper part by forcing a pressure medium through said vertical part and into the upper part so as to expand the upper part and thereby substantially uniformly a portion of the vessel in said joint area, wherein said pressurizing step expands said vessel to provide additional surface area of vessel material;
    depressurizing the upper part by removing the pressure medium from the upper part, allowing the upper part to return to its unexpanded state; and
    removing the upper part of said T-shaped member from said vessel.

2. The method of claim 1, wherein the step of depressurization comprises evacuating the upper part causing the upper part to collapse to a size smaller than its original unexpanded state.

3. The method of claim 1, wherein said pressurizing step comprises expanding the upper part of the T-shaped member to approximately twice its unexpanded size.

4. The method of claim 1, wherein the pressure medium is provided to the T-shaped member by means of a syringe attached to an end of the vertical part.

5. The method of claim 3, wherein the upper part of the T-shaped member is approximately 2 millimeters in diameter and approximately 8 millimeters in length.

* * * * *

UNITED STATES PATENT AND TRADEMARK OFFICE
CERTIFICATE OF CORRECTION

PATENT NO. : 5,036,868

DATED : August 6, 1991

INVENTOR(S) : Berggren et al.

It is certified that error appears in the above-identified patent and that said Letters Patent is hereby corrected as shown below:

Column 4, line 8, after the word "uniformly", insert the word --expand--.

Signed and Sealed this

Second Day of March, 1993

Attest:

STEPHEN G. KUNIN

Attesting Officer

Acting Commissioner of Patents and Trademarks